United States Patent [19]

Boyajian

[11] 4,319,877
[45] * Mar. 16, 1982

[54] PALLADIUM-BASED DENTAL ALLOY CONTAINING INDIUM AND TIN

[76] Inventor: Benjamin K. Boyajian, 309 Alderman Rd., Charlottesville, Va. 22903

[*] Notice: The portion of the term of this patent subsequent to Apr. 14, 1998, has been disclaimed.

[21] Appl. No.: 180,143

[22] Filed: Aug. 21, 1980

Related U.S. Application Data

[63] Continuation-in-part of Ser. No. 83,344, Oct. 10, 1979, Pat. No. 4,261,744.

[51] Int. Cl.³ .......................... A61K 6/04; C22C 5/04
[52] U.S. Cl. .................................. 433/207; 75/172 R
[58] Field of Search .............. 75/172 R; 433/200, 207

[56] References Cited

U.S. PATENT DOCUMENTS

| | | | |
|---|---|---|---|
| 1,999,866 | 4/1935 | Capillon et al. | 75/172 |
| 2,074,996 | 3/1937 | Cohn | 75/172 |
| 2,105,312 | 1/1938 | Cohn | 75/172 R |
| 2,143,217 | 1/1939 | Truthe | 75/172 |
| 2,781,580 | 2/1957 | Liebig | 433/200 |
| 3,029,475 | 12/1975 | Ingersoll | 75/172 |
| 3,424,577 | 1/1969 | Nielsen et al. | 75/134 |
| 3,574,611 | 4/1971 | Prosen | 75/165 |
| 3,679,402 | 7/1972 | Hirschhorn | 75/165 |
| 3,819,366 | 6/1974 | Katz | 75/172 R |
| 3,928,913 | 12/1975 | Schaffer | 75/172 R |
| 3,929,474 | 12/1975 | Ingersoll | 75/172 |
| 3,961,420 | 8/1976 | Tuccillo | 32/8 |
| 3,981,723 | 9/1976 | Tuccillo | 75/165 |
| 4,008,080 | 2/1977 | Wagner | 75/134 N |
| 4,123,262 | 10/1978 | Cascone | 75/165 |
| 4,124,382 | 11/1978 | Prosen | 75/172 |
| 4,179,286 | 12/1979 | Knosp | 75/134 N |
| 4,179,288 | 12/1979 | Prosen | 75/172 G |
| 4,194,907 | 3/1980 | Tsai | 75/134 N |
| 4,261,744 | 4/1981 | Boyajian | 75/172 |

OTHER PUBLICATIONS

Kosovinc et al., *Metall.*, vol. 26, 917–921 (1972).

*Primary Examiner*—L. Dewayne Rutledge
*Assistant Examiner*—Alan E. Schiavelli
*Attorney, Agent, or Firm*—Charlotte M. Kraebel

[57] ABSTRACT

A non-discoloring palladium-based alloy, free of silver or gold, suitable for fusion to dental porcelain compositions consists essentially of 75–85% by weight of Pd, 5–10% by weight of In, 5–10.5% by weight of Sn, up to 7.5% by weight of Co, Cr or Ni and up to 0.25% by weight of Si. Inclusion of 0.2–0.7% by weight of Ru improves the physical and mechanical properties of the alloy.

11 Claims, No Drawings

PALLADIUM-BASED DENTAL ALLOY CONTAINING INDIUM AND TIN

REFERENCE TO RELATED APPLICATION

This is a continuation-in-part of Boyajian, Ser. No. 083,344, filed Oct. 10, 1979, now U.S. Pat. No. 4,261,744, issued Apr. 14, 1981.

PRIOR ART STATEMENT

Fusion of dental porcelain to metal frames has been common practice for the past twenty years. Gold, alloyed with platinum, palladium, silver and minor base elements, was conventionally the primary frame component.

As gold prices have climbed, researchers and practitioners sought alternatives to gold. One approach was lowering the gold content and adding more palladium and/or silver; another was the use of non-precious metals, such as nickel-chrome alloys or cobalt-based alloys. Although non-precious metal alloys are widely used, their acceptability is limited by poor bond strength to porcelain and nickel sensitivity of many patients.

Another approach has been the use of palladium-silver alloys. These alloys have been limited acceptance because silver discolors porcelain dental fittings. Consequently, even minor amounts of silver are no longer used.

The use of a high Pd or Pd-Pt based dental casting alloy containing as non-precious components a major amount of Co and Co-Ni and minor amounts of In or Sn is disclosed by Schaffer in U.S. Pat. No. 3,928,913. Although these alloys can be pickled with HCl to a white coloration, the normal color of oxide-coated alloy workpieces is gray. It will be apparent that discoloration can occur under thin areas of porcelain at the marginal region of a tooth and that the discoloration is aesthetically unacceptable. Moreover, even when a dark-appearing alloy inside of a tooth will be covered with cement, many dentists prefer to work with alloys which are light in appearance. These alloys are generally harder than A.D.A. Type IV alloys and are therefore difficult to cut and grind. In addition, the alloys described by Schaffer tend to absorb gases and produce highly porous castings.

The use of high concentrations of Pd in alloys for dental applications is disclosed by Cohn in U.S. Pat. Nos. 2,074,996 and 2,105,312 and by Prosen in U.S. Pat. No. 4,124,382. Cohn discloses Ni, to a maximum of 9%, and Ru, to a maximum of 9%, as alloying elements. Prosen indicates the use of Sn, Fe, Al and B as required additives and of Ru as an optional additive.

Kosovinc et al., Metall, Vol. 26 (9), (1972) at 917-920, disclose ternary alloys of Pd, Sn and In.

Alloys containing Au or Ag, in addition to Pd, are set forth in the following U.S. Pat. Nos.:
1,999,866—Capillon et al
3,424,577—Nielsen et al
3,574,611—Prosen
3,679,402—Hirschhorn
3,819,366—Katz
3,929,474—Ingersoll
3,929,475—Ingersoll
3,961,420—Tuccillo
3,981,723—Tuccillo
4,008,080—Wagner
4,123,262—Cascone
4,179,286—Knosp
4,179,288—Prosen
4,194,907—Tsai It is apparent that there is a continuing need for low cost gold-free alloys, which do not discolor because of their silver content, which are easy to fabricate and which are compatible with and adhere firmly to porcelain formulations used in dental prosthesis.

OBJECT OF THE INVENTION

It is an object of the invention to provide a palladium alloy, containing neither silver nor gold, which has the properties of an alloy of high nobility but is much lower in cost than a gold-based alloy. Because palladium costs about half of what gold costs in present day markets and is much lower in density than gold, the alloys of the invention provide a significant economic advantage over gold without loss of desired characteristics.

SUMMARY OF THE INVENTION

In a compositional aspect this invention relates to an alloy consisting essentially of 75-85% by weight of Pd, 5-10.5% by weight of In, 5-10.5% by weight of Sn, up to 7.5% by weight of Co, Cr or Ni and up to 0.25% by weight of Si, as well as to alloys containing 0.2-0.7% by weight of Ru.

In a clinical aspect, this invention relates to a dental prosthesis comprising a cast palladium alloy base, the alloy consisting essentially of 77-82% by weight of Pd, 7.5-10.5% by weight of In, 7.0-10.0% by weight of Sn, 1.0-7.5% by weight of Co and 0.1-0.25% by weight of Si, in the shape of a tooth and a porcelain coating firmly adhered to at least a portion of the cast palladium alloy base. It further relates to prosthesis in which the alloy base contains 0.2-0.7% by weight of Ru.

DETAILED DESCRIPTION

Alloys are made by combining the weighed metallic components in a crucible and melting in a vacuum furnace. The molten material is held in the liquid state for 2 minutes and then cooled rapidly at a rate of about 100° F./min (55° C./min) to room temperature. The product is in the form of ingots.

It is preferred that the alloys of this invention contain at least 1% by weight of Co, Cr or Ni. More preferably, the alloys of this invention will contain Pd, In, Sn, Co and at least 0.01% by weight of Si and 0.2% by weight of Ru. More preferably, the Pd content is 77-82% by weight. Most preferably, the alloys contain 77-82% by weight of Pd, above 7.5% by weight of In, above 7.0% by weight of Sn, above 0.2% by weight of Ru and more than 0.1% by weight of Si. Alloys of the foregoing compositions may be used for routine crown and bridge work, as well as for bonding to porcelain prostheses. However, alloys particularly adapted for porcelain bonding will contain at least 1.0%, preferably 4.0% by weight of Co to assure adequate hardness. Hardness was determined by the Vickers microhardness test, also known as the Diamond Hardness Test (DPN).

Alloys made in accordance with the invention melt in the range below 1375° C., but the preferred alloys melt at 1150°-1375° C. and have a coefficient of thermal expansion compatible with that of porcelain used for dental restoration or prosthesis, which is generally $14-16 \times 10^{-6}$/°C.

It will be understood that, although the coefficient of thermal expansion of the alloys of this invention can be measured by dilatometry, there is not inevitably an exact correlation between the measured coefficient of thermal expansion and behavior in a dental laboratory. Accordingly, the following qualitative criteria can be used as a practical test of compatibility between the alloy and the porcelain of a dental prosthesis:

(1) no porcelain cracking is observed as a result of cooling the prosthesis from the fusion temperature or of refiring the prosthesis;
(2) no cracks are observed around small or large pontics;
(3) no cracks are observed in any single unit or multiple unit splint, including a full arch splint of 14 teeth;
(4) no cracks occur upon repeated refiring;
(5) no cracks occur as a result of heavy grinding of the porcelain;
(6) no cracks occur upon post-soldering of the prosthesis;
(7) no cracks occur following hard tapping of the prosthesis with a metal instrument, e.g., a hammer.

Addition of silicon to the alloys of this invention decreases absorption of gases by the molten alloy and, at the preferred levels of 0.10–0.25% by weight of Si, completely prevents gas absorption. The resulting alloys are not porous because of gases trapped therein and adhere more firmly to dental porcelain than porous alloys. However, inclusion of more than 0.25% by weight of Si in the alloys produce a cast product which contains cracks and voids.

Inclusion of the specified amounts of ruthenium in the alloys of this invention results in grain refinement so as to eliminate a casting defect known as "hot tearing". Alloys containing ruthenium also have physical and mechanical properties superior to those of alloys containing none. Most preferably, the Ru level is 0.3–0.5% by weight.

In addition to their superiority in appearance over dark-appearing alloys containing silver or high amounts of non-precious metals, the alloys of the present invention permit oxide formation sufficient to attain good bonding to porcelain, but low enough to avoid weakening encountered at high oxide levels.

The porcelains which can be bonded to the alloys of this invention are, for example, those based on feldspar, nepheline or a crystalline constituent of leucite, as disclosed by Schaffer, supra, incorporated herein by reference. It will be understood that any porcelain having a coefficient of thermal expansion about the same as the alloy being employed can be used.

A technique suitable for making dental restorations is described in Tucillo '420, supra, incorporated herein by reference. As indicated by the Tucillo reference, "compatibility" between alloy and porcelain means that each has essentially matching coefficients of thermal expansion, that of the porcelain preferably being slightly less than that of the alloy. In using the alloys of this invention, a slightly broader opaque firing range can be used, about 955°–1010° C.

Alloys of this invention become firmly bonded to the porcelain portion of the reconstruction during the heat treatment, preferably by chemical and diffusion bonding.

The alloys of this invention have properties meeting criteria for bridgework, defined by ADA specification no. 5, Types III and IV. Generally, alloys containing higher amounts of Co, above about 4.0%, meet type IV standards. Alloys of this type can be used for long span bridgework, of five units or above.

DESCRIPTION OF PREFERRED EMBODIMENTS

For general use, preferred alloys are those consisting essentially of 77–82% by weight of Pd, 7.5–10.5% by weight of In, 7.0–10.5% by weight of Sn, 0.2–0.7% by weight of Ru, up to 7.5% by weight of Co and 0.1–0.25% by weight of Si, and having a melting point of 1150°–1375° C.

For use in dental restorations, preferred alloys consist essentially of 77–82% by weight of Pd, 7.5–10.5% by weight of In, 7-0–10.0% by weight of Sn, 4.0–7.5% by weight of Co, 0.2–0.7% by weight of Ru, and 0.1–0.25% by weight of Si and have a melting point of 1150°–1375° C. In a most preferred embodiment, the prosthesis will be made of the corresponding alloys, the porcelain coating being firmly adhered to the alloy by chemical and diffusion bonding.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius. Unless otherwise indicated all parts and percentages are by weight.

EXAMPLES 1–7

Alloys of the compositions indicated below were made by combining the indicated components in a crucible and melting in a vacuum furnace at about 1400° C. The melt was kept in the liquid state for about an hour and poured into ingot molds which were cooled at a rate of about 55° C./min to give ingots. Properties of the products are given in the Table below:

| Example | % by weight | | | | | Properties | |
| | Pd | In | Sn | Co | Si | Vickers (DPN) | ADA type |
| --- | --- | --- | --- | --- | --- | --- | --- |
| (1) | 78.2 | 8.9 | 7.7 | 5.0 | .2 | 181 | IV |
| (2) | 79.5 | 8.4 | 8.4 | 3.5 | .2 | 140 | III |
| (3) | 80.2 | 9.1 | 9.0 | 1.5 | .2 | 115 | III |
| (4) | 81.9 | 7.8 | 10.2 | 0 | .1 | 89 | |
| (5) | 78.9 | 8.6 | 7.8 | 4.5 | .2 | 176 | IV |
| (6) | 77.2 | 8.9 | 7.7 | 6.0 | .2 | 192 | IV |
| (7) | 77.0 | 9.0 | 7.1 | 6.7 | .2 | 198 | IV |

The alloy containing no Co (Example 4) was relatively softer than the others and was judged unsuitable for use in porcelain-alloy restorations. It is useful for onlays and routine crown and bridge work.

Any of the other alloys was judged acceptable for use in porcelain-alloy prosthesis, but those containing more than about 4.0% by weight of Co and being of A.D.A. Type IV (Examples 1, 5, 6 and 7) are preferred for this purpose.

EXAMPLE 8

The alloy of Example 1 is fabricated into a tooth restoration as described by Tucillo '420, using a temperature of 955°–1010° C. for the opaquing step. The porcelain employed was Vita, obtained from Unitek Corporation, 2724 South Peck Rd., Monrovia, Calif. 91016.

An acceptable restoration was obtained, that is, the bonding was well opaqued and no bubble formation was noted. No crazing or blistering of the porcelain was observed. The prosthesis had the same attributes as a restoration made from porcelain and gold alloys.

EXAMPLE 9

Alloy prepared as in Example 5 was used to prepare a tooth restoration containing an alloy based in the shape of a tooth, firmly bonded to Vita porcelain. The restoration was acceptable to the dental trade, compatibility between the alloy and porcelain meeting the criteria described above.

EXAMPLE 10

Alloys are prepared as in Example 1, substituting Ni or Cr for Co. The properties of the alloys obtained are similar to those of the alloys containing Co.

EXAMPLES 11-13

Alloys including ruthenium for grain refinement were prepared as in Examples 1-7 from the following components:

| Example | % by weight | | | | | |
|---|---|---|---|---|---|---|
| | Pd | In | Sn | Co | Si | Ru |
| 11 | 78.0 | 8.9 | 7.7 | 5.0 | 0.2 | 0.2 |
| 12 | 77.7 | 8.9 | 7.7 | 5.0 | 0.2 | 0.5 |
| 13 | 77.5 | 8.9 | 7.7 | 5.0 | 0.2 | 0.7 |

The alloys had the following properties:

| | Example 11 | Example 12 |
|---|---|---|
| hardness: Vicker's (DPN) | 218 | 224 |
| ultimate tensile strength (psi) | 122,837 | 123,390 |
| yield strength (psi) | 92,000 | 94,000 |
| elongation (%) | 7-12 | 5-10 |
| melting range (°C.) | 1316-1372 | 1316-1372 |
| grain size (microns) | 100-150 | ~50 |

EXAMPLE 14

Alloy of the composition recited in Example 12 is used to prepare a tooth restoration containing an alloy base in the shape of a tooth and bonded firmly to Vita porcelain. The restoration is of a quality acceptable to the dental profession.

EXAMPLE 15

Alloys are prepared as in Examples 11-13, substituting Ni or Cr for Co. The properties of the alloys are similar to those of Co-containing alloys.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An alloy, free of gold or silver, consisting essentially of 75-85% by weight of Pd, 5-10.5% by weight of In, 5-10.5% by weight of Sn, 0.2-0.7% by weight of Ru, up to 7.5% by weight of Co, Cr or Ni and up to 0.25% by weight of Si.

2. The alloy of claim 1, consisting essentially of 77-82% by weight of Pd, 5-10.5% by weight of In, 5-10.5% by weight of Sn, 0.2-0.7% by weight of Ru, up to 7.5% by weight of Co and 0.01-0.25% by weight of Si.

3. The alloy of claim 1, consisting essentially of 77-82% by weight of Pd, 7.5-10.5% by weight of In, 7.0-10.5% by weight of Sn, 0.2-0.7% by weight of Ru, up to 7.5% by weight of Co and 0.01-0.25% by weight of Si.

4. The alloy of claim 1, consisting essentially of 77-82% by weight of Pd, 7.5-10.5% by weight of In, 7.0-10.5% by weight of Sn, 0.2-0.7% by weight of Ru, up to 7.5% by weight of Co and 0.1-0.25% by weight of Si.

5. The alloy of claim 1, consisting essentially of 77-82% by weight of Pd, 7.5-10.5% by weight of In, 7.0-10.0% by weight of Sn, 1.0-7.5% by weight of Co, 0.2-0.7% by weight of Ru and 0.1-0.25% by weight of Si.

6. The alloy of claim 1, consisting essentially of 77-82% by weight of Pd, 7.5-10.5% by weight of In, 7.0-10.0% by weight of Sn, 4.0-7.5% by weight of Co, 0.2-0.7% by weight of Ru and 0.1-0.25% by weight of Si.

7. The alloy of claim 1, having a melting point of 1150°-1375° C. and a coefficient of expansion compatible with dental porcelain.

8. The alloy of claim 4, having a melting point of 1150°-1375° C.

9. The alloy of claim 6, having a melting point of 1150°-1375° C.

10. A dental prosthesis comprising a cast palladium alloy base in the shape of a tooth, the palladium alloy being that of claim 5, and a porcelain coating firmly adhered to at least a portion of the cast palladium alloy base.

11. The dental prosthesis of claim 10, wherein the cast alloy consists essentially of 77-82% by weight of Pd, 7.5-10.5% by weight of In, 7.0-10.0% by weight of Sn, 4.0-7.5% by weight of Co, 0.2-0.7% by weight of Ru and 0.1-0.25% by weight of Si and has a melting point of 1150°-1375° C. and the porcelain coating is firmly adhered to the cast palladium alloy base by chemical and diffusion bonding.

* * * * *